(12) United States Patent
Jiang et al.

(10) Patent No.: US 10,494,630 B2
(45) Date of Patent: Dec. 3, 2019

(54) LINKER ELEMENT AND METHOD OF USING SAME TO CONSTRUCT SEQUENCING LIBRARY

(71) Applicant: MGI Tech Co., Ltd., Guangdong (CN)

(72) Inventors: Yuan Jiang, Shenzhen (CN); Chunyu Geng, Shenzhen (CN); Xia Zhao, Shenzhen (CN); Shujin Fu, Shenzhen (CN); Lingyu He, Shenzhen (CN); Yaqiao Li, Shenzhen (CN); Xiaoshan Su, Shenzhen (CN); Fanzi Wu, Shenzhen (CN); Wenwei Zhang, Shenzhen (CN); Hui Jiang, Shenzhen (CN); Andrei Alexeev, Woodland, CA (US); Radoje Drmanac, Mountain View, CA (US)

(73) Assignee: MGI TECH CO., LTD. (CN)

( * ) Notice: Subject to any disclaimer, the term of this patent is extended or adjusted under 35 U.S.C. 154(b) by 294 days.

(21) Appl. No.: 15/519,112

(22) PCT Filed: Oct. 14, 2014

(86) PCT No.: PCT/CN2014/088592
§ 371 (c)(1),
(2) Date: Apr. 13, 2017

(87) PCT Pub. No.: WO2016/058136
PCT Pub. Date: Apr. 21, 2016

(65) Prior Publication Data
US 2017/0233728 A1 Aug. 17, 2017

(51) Int. Cl.
*C12N 15/10* (2006.01)
*C12Q 1/68* (2018.01)
(Continued)

(52) U.S. Cl.
CPC ....... *C12N 15/1093* (2013.01); *C12N 9/1205* (2013.01); *C12N 9/1252* (2013.01);
(Continued)

(58) Field of Classification Search
CPC .. C12Q 1/6806; C12Q 1/6855; C12Q 1/6853; C12Q 2525/191; C12Q 1/68;
(Continued)

(56) References Cited

U.S. PATENT DOCUMENTS

2009/0176234 A1* 7/2009 Drmanac ............. C12Q 1/6855
435/6.12
2011/0281736 A1 11/2011 Drmanac et al.

FOREIGN PATENT DOCUMENTS

CN 101532014 A 9/2009
CN 103667273 A 3/2014
(Continued)

OTHER PUBLICATIONS

NEB (USER™ Enzyme) (Year: 2013).*
(Continued)

*Primary Examiner* — Jeremy C Flinders
(74) *Attorney, Agent, or Firm* — McDonald Hopkins LLC (57) ABSTRACT

Provided is a linker element and a method of using the linker element to construct a sequencing library, wherein the linker element consists of a linker A and a linker B, the linker A is obtained through the complementary pairing of a long nucleic acid strand and a short nucleic acid strand, the 5' end of the long strand has a phosphoric acid modification, and the 3' end of the short strand has an enclosed modification, with enzyme sites in the short strand; and the linker B is a nucleic acid single strand, and the 3' end thereof can be in a complementary pairing with the 5' end of the long strand of the linker A. Using the linker element of the present invention for constructing a sequencing library ensures the
(Continued)

linking directionality of the linkers while solving the problems of fragment interlinking, linker self-linking and low linking efficiency, and reducing the purification reaction between steps, shortening the linking time and reducing costs.

7 Claims, 2 Drawing Sheets

Specification includes a Sequence Listing.

(51) Int. Cl.
| | |
|---|---|
| *C12N 15/11* | (2006.01) |
| *C40B 40/06* | (2006.01) |
| *C12N 9/12* | (2006.01) |
| *C12N 9/16* | (2006.01) |
| *C12Q 1/6806* | (2018.01) |
| *C12Q 1/6855* | (2018.01) |
| *C40B 50/06* | (2006.01) |

(52) U.S. Cl.
CPC ............ *C12N 9/16* (2013.01); *C12N 15/11* (2013.01); *C12Q 1/68* (2013.01); *C12Q 1/6806* (2013.01); *C12Q 1/6855* (2013.01); *C12Y 207/01078* (2013.01); *C12Y 207/07007* (2013.01); *C12Y 301/03001* (2013.01); *C40B 40/06* (2013.01); *C40B 50/06* (2013.01); *C12Q 2525/191* (2013.01)

(58) Field of Classification Search
CPC ...... C12N 9/1205; C12N 9/1252; C12N 9/16; C12N 15/1093; C12N 15/11; C12Y 207/01078; C12Y 207/07007; C12Y 301/03001; C40B 40/06; C40B 50/06
See application file for complete search history.

(56) References Cited

FOREIGN PATENT DOCUMENTS

| WO | WO-2013/112923 A1 | 8/2013 |
|---|---|---|
| WO | 2015134552 | 9/2015 |

OTHER PUBLICATIONS

Mertes, F. et al., "Targeted enrichment of genomic DNA regions for next-generation sequencing." Briefings in Functional Genomics. vol. 10 No. 6, 374-386, (2011).

International Search Report dated May 29, 2015, for PCT/CN2014/088592, filed on Oct. 14, 2014, and English translation of the same, 7 pages.

Extended European Search Report for Application 14904072.7, PCT/CN2014/088592, dated May 17, 2018, 7 pgs., European Patent Office, Germany.

\* cited by examiner

FIG. 1

FIG. 2

SEQUENCE LISTING

<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Terminal phosphate group modification

<400> SEQUENCE: 1
gtctccagtc tcaactgcct gaagcccgat cgagcttgtc t                    41

<210> SEQ ID NO 2
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 11
<223> OTHER INFORMATION: n = dideoxycytidine

<400> SEQUENCE: 2
gacuggagac n                                                     11

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
tcctaagacc gcactggaga c                                          21

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Terminal phosphate group modification

<400> SEQUENCE: 4
agacaagctc gatcgggctt c                                          21

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
tcctaagacc gcactggaga c                                          21

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
gaagcccgat cgagcttgtc t                                          21

<210> SEQ ID NO 7
<211> LENGTH: 10
<212> TYPE: DNA
<213> ORGANISM: Artificial Sequence
<220> FEATURE:
<223> OTHER INFORMATION: Synthetic Construct

```
<400> SEQUENCE: 7
gtctccagtc                                                                    10

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
gtctccagtg cggtcttagg a                                                       21

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: Terminal biotin modification

<400> SEQUENCE: 9
tcctaagacc gcactggaga c                                                       21

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
tcgagcttgt cttcctaaga ccgc                                                    24
```

LINKER ELEMENT AND METHOD OF USING SAME TO CONSTRUCT SEQUENCING LIBRARY

CROSS-REFERENCE TO RELATED APPLICATIONS

This application is a National Phase application under 35 U.S.C. § 371 of International Application No. PCT/CN2014/088592, filed on Oct. 14, 2014, the contents of which are hereby incorporated herein by reference in their entirety.

TECHNICAL FIELD

The present invention relates to the field of biotechnology and, in particular, to a linker element, a method of constructing a sequencing library using the linker element, the constructed sequencing library and application thereof.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 774972000100SEQLIST.txt, date recorded: Apr. 13, 2017, size: 3 KB).

BACKGROUND ART

High-throughput sequencing has become one of the foundations for modern molecular biology, biotechnology, medicine and other fields. In recent years, studies on rapid, accurate and economic methods for determining gene expression level and nucleotide sequence have achieved continuous innovation; the second generation of high-throughput sequencing technology with sequencing by synthesis as the basic principle has become mature. The major sequencing companies have focused on the development of new sequencing products, shortening the process of sequencing and cost reduction. The currently existing sequencing products based on the second-generation sequencing technology include whole genome resequencing, whole transcriptome sequencing, and small-molecule RNA sequencing and the like. In particular, the application derived from the second-generation sequencing combined with microarray technology—target sequence capture sequencing technology can use a large number of oligonucleotide probes to complementarily bind to specific regions in the genome to capture and enrich gene fragments from the specific regions for sequencing; and for the detection, diagnosis and research of disease genes.

Complete Genomics (CG) Corporation currently has an independently developed second-generation sequencing technology suitable for human whole genome sequencing. The process for its library construction includes: genomic DNA disruption, the first linker ligation, double-strand cyclization and digestion, the second linker ligation, single-strand separation and cyclization, wherein the two linker ligations are very important in the process for library construction. The linker is a specially designed DNA sequence and when fixed to both ends of the DNA fragment by ligation or the like, can be identified during sequencing and used as a starting site for sequencing to enable the instrument to read the subsequent sequence information. In order to ensure that the read sequence information is easy to analyze, it is necessary to add two different linkers at both ends (5' and 3' ends) of a DNA fragment; in order to achieve this particular directional ligation, while avoiding the interconnection between the linkers, sticky end can be used to link the linkers; however, this requires fragments with sticky ends, which make it difficult to avoid the interconnection between fragments. The Complete Genomics Corporation uses multiple steps to add linkers to both ends respectively for construction of a sequencing library. In order to obtain a fragment with linkers at both ends, it is necessary to go through the following five steps: ligating a linker to one end of a DNA fragment; performing denaturation, annealing and extension; then ligating a linker to the other end of the DNA fragment; filling the vacancy; and performing a polymerase chain reaction. However, the multiple extension reactions therein require expensive reagents and multiple purification steps are required between the steps, thus resulting in high overall costs and lack of efficiency.

In order to solve the problems that too many steps are required for linker ligation in the construction of the sequencing platform library of Complete Genomics, the time for constructing the whole library is too long and the cost is too high, the present invention is proposed.

SUMMARY

In view of the above disadvantages of the prior art, it is an object of the present invention to provide a linker element, a method of constructing a sequencing library using the linker element, the constructed sequencing library and application thereof. The method for constructing the sequencing library of the present invention avoids the conventional linker ligation method that adds linkers to both ends respectively in multi-steps. By means of a linker with a unique sequence configuration, and a novel linker ligation method consisting of linker ligation plus single strand replacement, the method for constructing the sequencing library of the present invention ensures the directionality of the linker ligation while solving the problems of fragment interconnection, linker self-connection and low ligation efficiency, and successfully reduces the whole linker ligation process to four new steps and reduces the purification reactions between steps, which greatly reduce the time required for ligating the linkers, and significantly reduce costs. In addition, the method of constructing a sequencing library also introduces the nucleic acid probe capture technology to realize the sequencing of the target genomic region, and succeeds in creating a target region capture sequencing product based on a single strand circular sequencing platform.

In a first aspect, the present invention provides a linker element consisting of a linker A and a linker B, wherein the linker A is generated from the complementary pairing of a long strand of nucleic acid and a short strand of nucleic acid, wherein the long strand has a phosphate modification at the 5' end and the short strand has a blocking modification at the 3' end, and has an enzyme active site in the short strand; and the linker B is a single-stranded nucleic acid, and the 3' end thereof can be complementary to the 5' end of the long strand of the linker A but the rest part cannot be complementary to the linker A.

Preferably, in the linker A, the long strand has a length of 40-48 bp and the short strand has a length of 9-14 bp.

Preferably, in the linker B, the length complementary to the long strand of the linker A is 6-12 bp, and the length not complementary to the long strand of the linker A is 9-15 bp.

Preferably, the blocking modification is a dideoxy blocking modification.

Preferably, the enzyme active site in the short strand is U or dU, and the corresponding enzyme is User enzyme.

Preferably, the linker B has a tag sequence; due to the presence of the tag sequence, in the subsequent steps, different samples with different tags can be mixed and placed in the same reaction system for reaction, further saving operating steps and cost.

In one preferred embodiment, the sequence of the long strand of the linker A is: /Phos/GTCTCCAGTCTCAACT-GCCTGAAGCCCGATCGAGCTTGTCT (i.e., SEQ ID NO: 1), the sequence of the short strand of the linker A is GACUGGAGAC/ddC/(i.e., SEQ NO: 2), the sequence of the linker B is TCCTAAGACCGCACTGGAGAC (i.e., SEQ ID NO: 3), wherein the group inside "//" represents terminal modified group, "Phos" represents phosphorylation and "dd" represents dideoxy.

In a second aspect, the present invention provides a linker ligation method, comprising ligating a linker element as described in the first aspect to both ends of a DNA fragment to be tested.

Preferably, the linker ligation method comprises the following steps:

(1) the linker A is added to both ends of the DNA fragment to be tested by a ligation reaction;

(2) the DNA fragment ligated with the linker A is treated with a corresponding enzyme according to the enzyme active site in the short strand;

(3) the linker B is added to both ends of the DNA fragment ligated with the linker A and treated in the step (2) by a ligation reaction.

Preferably, the steps of dephosphorylating and blunt-end repairing the DNA fragment to be tested are further comprised before ligating the linker element; in the step (2), it is further preferred that the step of phosphorylating the unlinked 5' end of the DNA fragment is further included, and it is further preferred that the phosphorylation treatment is carried out using a polynucleotide kinase.

In a third aspect, the present invention provides a method for constructing a sequencing library, which uses the linker element as described in the first aspect or the linker ligation method as described in the second aspect to perform linker ligation.

In a preferred embodiment, the method for constructing a sequencing library comprises the steps of:

1) fragmenting the DNA to be tested;

2) dephosphorylating and blunt-end repairing the DNA fragments obtained in step 1);

3) linker ligations:

linker A ligation: the linker A is added to both ends of the DNA fragments obtained in Step 2) by a ligation reaction;

enzyme treatment and phosphorylation: depending on the enzyme active site in the short strand of the A linker, the DNA fragments ligated with the linker A are treated with the corresponding enzyme, and the unlinked 5' ends of the fragments are phosphorylated; linker B ligation: through a ligation reaction, the linker B is added to both ends of the DNA fragments ligated with the linker A;

4) amplification of DNA fragments: polymerase chain reaction is carried out by using the DNA fragments obtained in step 3) as a template and using single-stranded nucleic acids C and D, which are complementary to the long strand of the linker A and the nucleic acid strand of the linker B, as primers;

5) hybridization capture: the product obtained in step 4) is captured by hybridizing with an oligonucleotide probe and in the enrichment step of the hybridization product, a separation marker is introduced at the 5' end of one strand of the double-stranded nucleic acid and a phosphate group modification is introduced at the 5' end of the other strand;

6) separation and cyclization of single-stranded nucleic acids: the product obtained in step 5) is separated by utilizing the separation marker to obtain another nucleic acid single strand without the separation marker; and a single strand circular nucleic acid product is obtained by cyclizing the obtained nucleic acid single strand, that is the sequencing library.

Regarding the above method for constructing a sequencing library:

In step 1), preferably, the DNA to be tested is genomic DNA.

Preferably, the fragmentation is a random disruption of the DNA to be tested using a physical or chemical method.

Preferably, the fragmentation of the DNA to be tested is performed by using physical ultrasound or enzymatic reaction.

Preferably, the length of the DNA fragment is 150-250 bp.

In step 2), preferably, the dephosphorylation is carried out by using alkaline phosphatase, preferably shrimp alkaline phosphatase.

Preferably, the blunt-end repair is performed by using T4 DNA polymerase.

In a preferred embodiment, the sequence of the long strand of the linker A in step 3) is /Phos/GTCTCCAGTCT-CAACTGCCTGAAGCCCGATCGAGCTTGTCT (i.e., SEQ ID NO: 1), the sequence of the short strand of the linker A is GACUGGAGAC/ddC/ (i.e., SEQ ID NO: 2), and the sequence of the linker B is TCCTAAGACCGCACTGGA-GAC (i.e., SEQ ID NO: 3), wherein the group in "//" is a terminal modified group, "Phos" represents phosphorylation, and "dd" represents dideoxy. In a further preferred embodiment, in step (4), the sequence of the single-stranded nucleic acid C is /Phos/AGACAAGCTCGATCGGGCTTC (i.e., SEQ ID NO: 4), the sequence of the single-stranded nucleic acid D is TCCTAAGACCGCACTGGAGAC (i.e., SEQ ID NO: 5), wherein the group in "//" is a terminal modified group, "Phos" represents phosphorylation.

In step 5), preferably, the oligonucleotide probe is a library of oligonucleotide probes; the hybridization capture step using an oligonucleotide probe allows the sequencing library of the present invention to achieve full exome sequencing. Further, by changing the oligonucleotide probe used, other different sequencing requirements can be met.

Preferably, the separation marker is a biotin modification.

In step 6), preferably, the step of removing the remaining uncyclized single strands by treatment with an exonuclease or the like is also included after cyclization of the single-stranded nucleic acid.

The single-stranded circular nucleic acid product obtained by the above-mentioned construction method can be used directly in the subsequent sequencing step in which the single-stranded circular nucleic acids are subjected to rolling replication to form nucleic acid nanospheres (DNB) for reading nucleic acid sequence information.

In a fourth aspect, the present invention provides a sequencing library, which is prepared by the construction method as described in the third aspect.

In a fifth aspect, the present invention provides the use of the sequencing library as described in the fourth aspect for genomic sequencing, preferably for sequencing of a target genomic region; preferably, the sequencing is performed by using a single-stranded circular library sequencing platform; more preferably, the sequencing is performed by using sequencing platform of Complete Genomics.

In a sixth aspect, the present invention provides a nucleic acid sequencing method comprising the step of sequencing the sequencing library as described in the fourth aspect; preferably, the sequencing is performed by using a single-stranded circular library sequencing platform; further preferably, the sequencing is performed by using sequencing platform of Complete Genomics; preferably, the method further comprises the step of assembling and/or splicing the sequencing results.

In a seventh aspect, the present invention provides a sequencing library construction kit comprising a linker element as described in the first aspect.

Preferably, the kit further comprises a dephosphorylase, preferably an alkaline phosphatase, more preferably a shrimp alkaline phosphatase; a DNA polymerase, preferably a T4 DNA polymerase; a User enzyme; and a phosphorylase, preferably a polynucleotide kinase.

Beneficial Effect

After the treatment in step 2), wherein the target nucleic acid fragment undergoes the terminal-blocking treatment of dephosphorylation, the fragmented DNA to be tested becomes a blunt-end fragment with both ends blocked, so that the interaction between the fragments is completely prevented, and thus the utilization of DNA fragments prior to ligation is extremely highly guaranteed.

The present invention introduces a phosphate group at the 5' end of the long strand of the linker A and a blocking modification at the 3' end of the short strand of the linker A. The blocked end cannot be ligated with the target nucleic acid fragment due to the presence of the blocking modification. Due to the special construction of the long and short strands themselves, there is no interconnection between the linkers, thus ensuring that the 5' end of the long strand of the linker can be accurately attached to the 3' end of the target fragment. This design is very effective in preventing the occurrence of linker interconnection, ensuring the efficiency of the ligation reaction.

Figure 1:
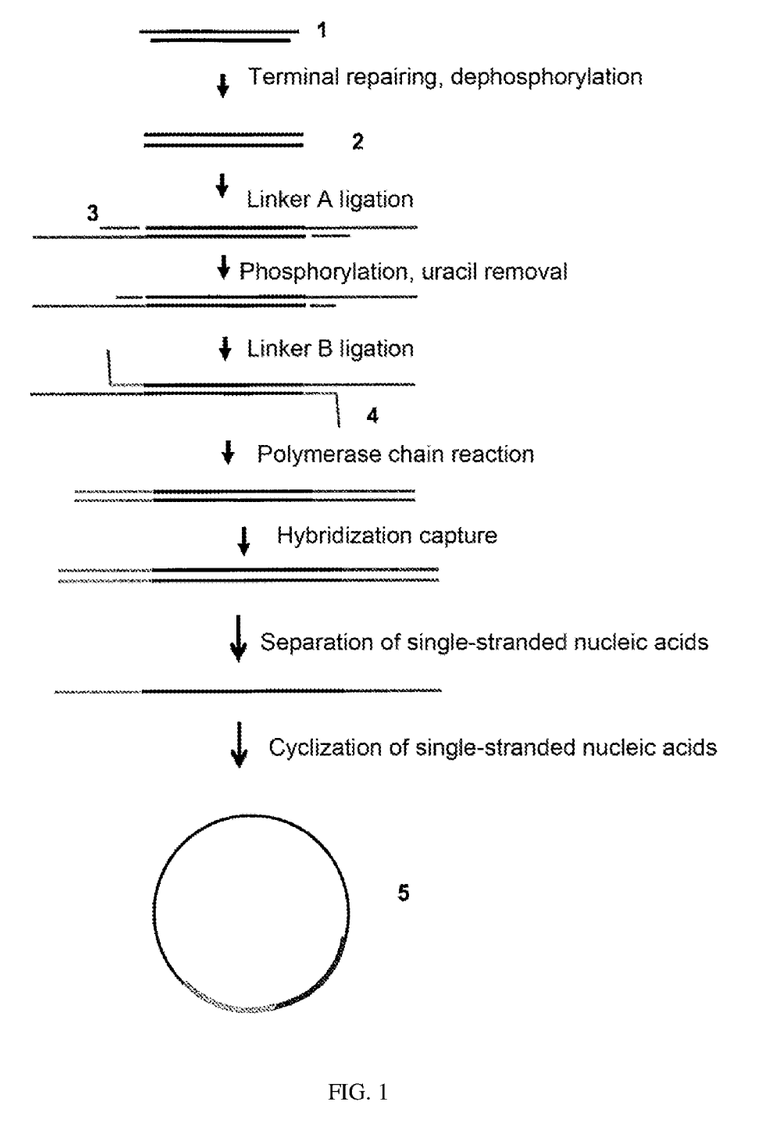
FIG. 1 illustrates a sequencing library construction scheme of the present invention; 1 represents a disrupted DNA fragment, 2 represents a dephosphorylated, terminal-repaired fragment (each terminal is a hydroxyl group), 3 represents the long and short strands of the linker A, 4 represents the single strand of the linker B, and 5 represents a library construction final product of nucleic acid single strand loop.
Figure 2:
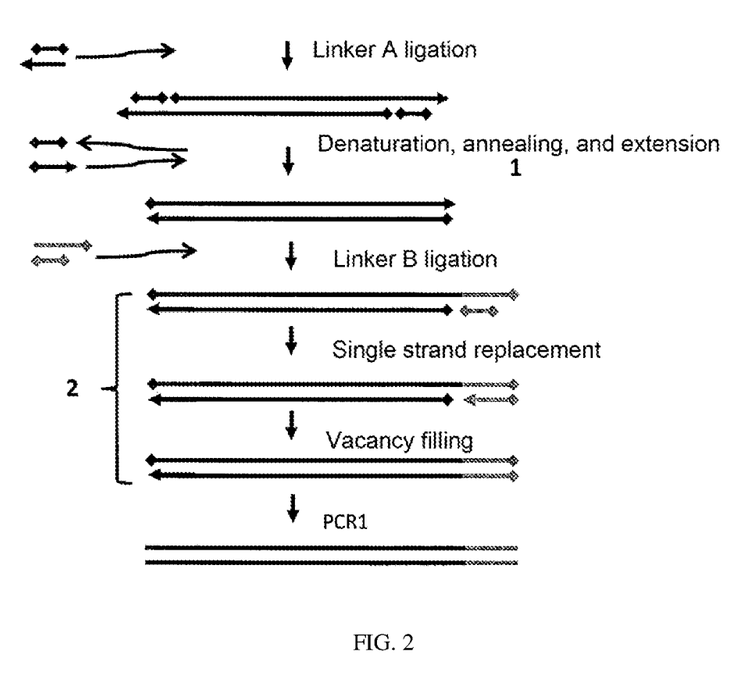
FIG. 2 illustrates the conventional linker ligation method of Complete Genomics; 1 represents the treatment step between the ligations of linker A' and B'; 2 represents three steps related to linker B' ligation.

In the target fragment phosphorylation step as designed to perform following the ligation of linker A, one end of the target fragment which is not linked to linker is phosphorylated. The short strand of the linker A is shortened and falls off during the enzymatic treatment after the ligation of the linker A, so that the linker B can be partially paired to the long strand of the linker A. The above all make it possible to orientate the linker B, and ensure the directionality of the linker ligation. In the conventional linker ligation step of Complete Genomics, after the ligation of linker A, denaturation, annealing and extension are performed to avoid ligating the same linker to both ends (as shown in FIG. 2, No. 1). Although this method also guarantees the directionality of the linker ligation, it needs to use high-fidelity hot-start enzyme, which incurs high cost, and long reaction time. However, the treatment enzymes (such as the User enzyme) used in the ligation method of the present invention are relatively inexpensive and require mild enzymatic reaction conditions, and the requirement to the reaction system is low, and the purification treatment step can be omitted before the enzyme treatment. Overall, the present invention reduces costs and processing time.

In the ligation of B linker, the characteristics of the short and long strands of linker A are also cleverly utilized. Since after the enzyme treatment, there are less and unstably bonded complementary pairing bases between the short strand and the long strand, the short strand will be separated from the long strand at relatively milder temperatures. The single strand of the linker B having a longer complementary base pairing sequence and a more dominant binding ability is simply complementary to the long strand of the linker A so that make it precisely linked to the vacant end of the target fragment. The other parts of the linker B that is not complementary ensure the differences between linker A and B. By subsequent polymerase chain reaction, the target fragment with different terminal sequences (i.e., the long strand of the linker A at one end, and the linker B at the other end) is ultimately formed. This unique design, in combination with polymerase chain reaction, solves the problems of cost-effective introduction of different linkers at both ends of the fragment in the blunt-end ligation. It also avoids the occurrence of fragment/linker interactions resulting from the ligation at cohesive end of the fragment produced by a step of introducing adenylate at terminal.

Compared with the traditional ligation method with linker B (shown in FIG. 2, No. 2) of Complete Genomics, this unique partially base-paired single strand linker design allows the linker ligation and vacancy fill-up to be replaced by a single step, greatly reducing the process and saving cost.

Based on the traditional sequencing library construction scheme of Complete Genomics, the present invention proposes a sequencing library construction scheme based on novel linker structure and linker ligation method, and introduces a probe hybridization capture step, so as to develop a novel target region capture library sequencing product based on the single-stranded circular library sequencing platform, realizing small region capture library sequencing based on the single-stranded circular library sequencing platform from scratch.

DETAILED DESCRIPTION

In order to facilitate understanding of the present invention, the present invention is exemplified as follows. It should be apparent to those skilled in the art that the described examples are merely to assist in understanding the present invention and should not be construed as limiting the invention thereto in any way.

EXAMPLE 1 Construction of a Sequencing Library of the Present Invention

1. Disruption of genomic DNA: There are many ways for genomic DNA disruption, such as physical ultrasound or enzymatic reaction, either of which has very mature schemes on the market. The present example employs a physical ultrasonic disruption method.

A Teflon line and 1 µg of genomic DNA were added into a 96-well PCR plate in turn, and then TE buffer solution or enzyme-free water was added to make up 80 µl. The plate was sealed and placed on an E220 ultrasonic disruption instrument. The conditions for disruption were set as follows:

| | |
|---|---|
| Filling coefficient | 20% |
| Severe degree | 5 |
| Pulse coefficient | 200 |
| Disruption time | 60 s, 5 times |

2. Recovery of disrupted fragments: magnetic beads purification method or gel recovery method can be used. Magnetic bead purification method was used in this example.

80 μl of Ampure XP magnetic beads were added into the disrupted DNA, and then mixed well and placed for 7-15 min; then the mixture was put into a magnetic frame, and the supernatant was collected and added 40 μl of Ampure XP beads, and then mixed well and placed for 7-15 min; then the mixture was put into the magnetic frame, then the supernatant was removed, and the magnetic beads were washed twice with 75% ethanol; after drying, the beads was added 50 μl of TE buffer solution or enzyme-free water, and then mixed well and placed for 7-15 min to dissolve the recovered product.

3. Dephosphorylation reaction: a system was prepared according the following table using the recovered products of the previous step:

| | |
|---|---|
| 10x NEB Buffer 2 | 2.4 μl |
| Shrimp alkaline phosphatase (1 U/ul) | 2.4 μl |
| Total | 4.8 μl |

4.8 μl of reaction system was added to the recovered product of the previous step, mixed, and a reaction was carried out under the conditions listed in the following table. The reaction product was used directly for the next step.

| | |
|---|---|
| 37° C. | 45 min |
| 65° C. | 10 min |

4. End repairing of fragments: a system was prepared according to the following table:

| | |
|---|---|
| Enzyme-free water | 4.9 μl |
| 10x NEB Buffer 2 | 0.72 μl |
| 0.1M adenosine triphosphate | 0.32 μl |
| 25 mM deoxyribonucleoside triphosphate | 0.32 μl |
| Bovine serum albumin | 0.16 μl |
| T4 deoxyribonucleic acid polymerase (3 U/ul) | 0.8 μl |
| Total | 7.2 μl |

After mixing, the system was added to the product of the previous step, mixed well and incubated at 12° C. for 20 min Purification was performed with 90 μl of Ampure XP magnetic beads and 18 μl of TE buffer solution was used to dissolve the recovered product. (There are many ways to purify the reaction product, such as magnetic bead method, column purification method, gel recovery method, etc. All the methods can be used interchangeably. The present example was purified by a magnetic bead method unless otherwise specified.)

5. Linker A ligation: The linker-related sequences used in this scheme were as follows (in the sequence, from left to right is the 5' end to the 3' end, the group inside "II" is terminal-modified group, "phos" represents phosphorylation, "dd" represents dideoxy, and "bio" represents biotin):

Long strand of the linker A:

/Phos/GTCTCCAGTCTCAACTGCCTGAAGCCCGATCGAGCTTGTCT (i.e., SEQ ID NO: 1);

Short strand of the linker A:

GACUGGAGAC/ddC/ (i.e., SEQ ID NO: 2);

The ligation buffer 1 used in this scheme was formulated as follows:

| | |
|---|---|
| Tris (hydroxymethyl) aminomethane-hydrochloric acid (pH 7.8) | 150 mM |
| Polyethylene glycol 8000 | 15% |
| Magnesium chloride | 30 mM |
| Ribonucleoside triphosphate | 3 mM |

A system was prepared as follows:

| | |
|---|---|
| Enzyme-free water | 11 μl |
| Linker A (100 uM) | 1 μl |
| Ligation buffer 1 | 13 μl |
| T4 DNA ligase (fast) (600 U/[mu]1) (enzymatics, L6030-HC-L) | 1 μl |
| Total | 21.5 μl |

The above system and the previous product were mixed and reacted according to the following table:

| | |
|---|---|
| 25° C. | 20 min |
| 65° C. | 10 min |

6. Phosphorylation and uracil removal: a system was prepared according to the following table:

| | |
|---|---|
| User enzyme (1000 U/ml) | 0.5 μl |
| Polynucleotide kinase (10 U/uL) | 0.5 μl |
| Total | 1 μl |

The above system was added to the product of step 5, mixed well and placed at 37° C. for 15 min.

Purification was performed by using 60 μl of Ampure XP magnetic beads, and 62.5 μl of enzyme-free water or TE buffer solution was used for recovery.

7. Linker B ligation:

The sequence of linker B was as follows:

TCCTAAGACCGCACTGGAGAC (i.e., SEQ ID NO: 3)

A system was prepared as follows:

| | |
|---|---|
| Ligation buffer 1 | 33 μl |
| T4 DNA ligase (fast) (600 U/ | 1 μl |

|  |  |
|---|---|
| [mu] 1) (enzymatics, L6030-HC-L) Linker B (100 uM) | 1.67 μl |
| Total | 37 μl |

The above system was added to the recovered product in step 6 and mixed well and reacted for 20 min at 20° C.

Purification was performed by using 120 μl of Ampure XP magnetic beads, and 45 μl of TE buffer solution was used to dissolve the recovered product.

8. Polymerase chain reaction:

The sequence of primer C was as follows:

/phos/AGACAAGCTCGATCGGGCTTC (i.e., SEQ ID NO: 4)

The sequence of primer D was as follows:

TCCTAAGACCGCACTGGAGAC (i.e., SEQ ID NO: 5)

A system was prepared as follows:

|  |  |
|---|---|
| enzyme-free water | 45 μl |
| 10x PfuTurbo Cx buffer (Agilent, 01.Agilent.600414) | 100 μl |
| PfuTurbo Cx hot-start nucleic acid polymerase (2.5 U/ul) (Agilent, 01.Agilent.600414) | 2 μl |
| 20 uM primer C | 4.0 μl |
| 20 uM primer D | 4.0 μl |
| Total volumn | 155.0 μl |

The recovered product in the previous step was added to the above system, mixed well, and then reacted according to the conditions listed in the following table:

|  |  |
|---|---|
| 95° C. | 3 min |
| 95° C. | 30 s |
| 56° C. | 30 s |
| 72° C. | 90 s |
| Steps 2-4 were repeated for 7 times |  |
| 68° C. | 7 min |

After completion of the reaction, 240 μl of Ampure XP magnetic beads were used for purification, and 25 μl of enzyme-free water was used to dissolve the recovered product.

9. Hybridization capture: 500 ng-1 μg of reaction product of the previous step was concentrated and evaporated, and then added to the following system 1 to dissolve:

Blocking Sequence 1:
GAAGCCCGATCGAGCTTGTCT (i.e., SEQ ID NO: 6)

Blocking sequence 2:
GTCTCCAGTC (i.e., SEQ ID NO: 7)

Blocking Sequence 3:
GTCTCCAGTGCGGTCTTAGGA (i.e., SEQ ID NO: 8)

|  |  |
|---|---|
| Enzyme-free water | 3.4 μl |
| SureSelect Block # 1 (Agilent) | 2.5 μl |
| SureSelect Block # 2 (Agilent) | 2.5 μl |
| Blocking sequence 1 | 0.3 μl |
| Blocking sequence 2 | 0.3 μl |
| Blocking sequence 3 | 0.3 μl |
| Total volume | 9.3 μl |

The mixed reaction system 1 was allowed to react at 95° C. for 5 minutes and kept at 65° C.

System 2 was prepared as follows:

|  |  |
|---|---|
| SureSelect Hyb # 1 (Agilent) | 8.3 μl |
| SureSelect Hyb # 2 (Agilent) | 0.3 μl |
| SureSelect Hyb # 3 (Agilent) | 3.3 μl |
| SureSelect Hyb # 4 (Agilent) | 4.3 μl |
| Total volume | 16.3 μl |

System 2 was added to System 1 and kept at 65° C.

System 3 was prepared as follows:

|  |  |
|---|---|
| Enzyme-free water | 1 μl |
| SureSelect RNase Block (Agilent) | 1 μl |
| SureSelect Oligo Capture Library | 5 μl |
| Total volume | 7 μl |

System 3 was added to the system 1 and 2, and reacted at 65° C. for 20-24 h.

After completion of the reaction, streptavidin-coated magnetic beads were used for binding, and the beads were dissolved in 50 ul of enzyme-free water after completion of the binding.

The following reaction system was prepared:

The sequence of primer D with biotin-modification was as follows:

/bio/TCCTAAGACCGCACTGGAGAC (i.e., SEQ ID NO: 9)

|  |  |
|---|---|
| Enzyme-free water | 40 μl |
| 10x PfuTurbo Cx buffer (Agilen, 01.Agilent.600414) | 100.0 μl |
| PfuTurbo Cx Hot Start Nucleic Acid Polymerase (2.5 U/ul) (Agilent, 01.Agilent.600414) | 2 μl |
| 20 uM primer C | 4 μl |
| 20 uM primer D (biotin-modification) | 4 μl |
| Total volumn | 150 μl |

The dissolved magnetic beads were added to the reaction system, mixed, and reacted according to the following table:

| | |
|---|---|
| 95° C. | 3 min |
| 95° C. | 30 s |
| 56° C. | 30 s |
| 72° C. | 90 s |
| 68° C. | 7 min |

After completion of the reaction, 240 μl of Ampure XP beads were used for purification. 80 μl of TE buffer solution or enzyme-free water was used for dissolving the recovered product.

10. Separation of the single-stranded nucleic acids: Streptavidin-coated beads were used to bind the biotin-containing target fragments obtained in Step 9. The single-stranded nucleic acids with no magnetic beads bound were separated by using 78 μl of 0.1 M sodium hydroxide, and the separated product was neutralized by the addition of an acidic buffer. The total volume of the neutralized product was 112 μl.

11. Cyclization of the single-strand nucleic acids: The following reaction system 1 was prepared: wherein the nucleic acid single strand E has a corresponding complementary sequence for ligating to both ends of the single strand. The sequence of single strand E was as follows:

TCGAGCTTGTCTTCCTAAGACCGC (i.e., SEQ ID NO: 10)

| | |
|---|---|
| Enzyme-free water | 43 μl |
| Nucleic acid single strand E | 20 μl |
| Total | 63 μl |

Reaction system 1 was added to the single strand product of step 10 and mixed.

Preparation of reaction system 2:

| | |
|---|---|
| Enzyme-free water | 153.3 μl |
| 10× TA buffer (epicenter) | 35 μl |
| 100 mM Adenosine triphosphate | 3.5 μl |
| T4 DNA Ligase (fast) (600 U/ul) (enzymatics, L6030-HC-L) | 1.2 μl |
| Total | 175 μl |

The reaction system 2 was added to the reaction system 1, mixed, and incubated at 37° C. for 1.5 h.

12. Treatment by Exonuclease 1 and Exonuclease 3:
Preparation of the following reaction buffer:

| | |
|---|---|
| Enzyme-free water | 1.5 μl |
| 10× TA buffer (Epicentre) | 3.7 μl |
| Exonuclease 1 (20 U/ul) (NEB Company, M0293S) | 11.1 μl |
| Exonuclease 3 (100 U/ul) (NEB Company, M0206S) | 7.4 μl |
| Total | 23.7 μl |

23.7 μl of the reaction buffer was added to 350 μl of the reaction product from Step 11, mixed well and incubated at 37° C. for 30 min.

15.4 μl of 500 mM ethylenediaminetetraacetic acid was added and mixed well. 800 μl of Ampure XP magnetic beads were used for purification and 40-80 μl of enzyme-free water/TE buffer was used for dissolving.

The concentrations and total amounts of the final products of the present example were as follows:

| | concentration (ng/μl) | Total amount (ng) |
|---|---|---|
| Product 1 | 0.40 | 16 |
| Product 2 | 0.42 | 16.8 |
| Product 3 | 0.48 | 19.2 |

Applicant declares that the present invention describes the detailed process equipment and process flow of the present invention by way of the above-described embodiments, however, the present invention is not limited to the detailed process equipment and process flow described above, that is to say, it does not imply that the present invention must rely on the above-described detailed process equipment and process flow. It should be apparent to those skilled in the art that any modification of the invention, equivalents of the ingredients of the product of the present invention, the addition of auxiliary ingredients, selection of specific modes, etc., fall within the disclosed scope and protective scope of the present invention.

The invention claimed is:

1. A method for constructing a sequencing library which uses a linker element consisting of a linker A and a linker B, wherein the linker A is generated from the complementary pairing of a long strand of nucleic acid and a short strand of nucleic acid, wherein the long strand has a phosphate modification at the 5' end and the short strand has a blocking modification at the 3' end, and has an enzyme active site in the short strand; and the linker B is a single-stranded nucleic acid, and the 3' end thereof can be complementary to the 5' end of the long strand of the linker A but the rest part cannot be complementary to the linker A, wherein the method comprises the steps of:
(1) fragmenting a DNA to be tested;
(2) dephosphorylating and blunt-end repairing the DNA fragments obtained in step 1);
(3) linker ligations:
linker A ligation: the linker A is added to both ends of the DNA fragments obtained in Step (2) by a ligation reaction;
enzyme treatment and phosphorylation: depending on the enzyme active site in the short strand of the A linker, the DNA fragments ligated with the linker A are treated with the corresponding enzyme, and the unlinked 5' ends of the fragments are phosphorylated; and
linker B ligation: through a ligation reaction, the linker B is added to both ends of the DNA fragments ligated with the linker A; and
(4) amplification of DNA fragments: polymerase chain reaction is carried out using the DNA fragments obtained in Step (3) as a template and using single-stranded nucleic acids C and D, which are complementary to the long strand of the linker A and the nucleic acid strand of the linker B, as primers,
upon which steps the sequencing library is obtained.

2. The method for constructing a sequencing library according to claim 1, further comprising the steps of:
(5) hybridization capture: the product obtained in Step (4) is captured by hybridizing with an oligonucleotide probe and in the enrichment step of the hybridization product, a separation marker is introduced at the 5' end of one strand of the double-stranded nucleic acid and a phosphate group modification is introduced at the 5' end of the other strand; and
(6) separation and cyclization of single-stranded nucleic acids: the product obtained in Step (5) is separated by utilizing the separation marker to obtain another nucleic acid single strand without the separation marker; and a single strand circular nucleic acid product is obtained by cyclizing the obtained nucleic acid single strand, that is the sequencing library.

3. The method for constructing a sequencing library according to claim 1, wherein in Step (2) the dephosphorylation is carried out by using shrimp alkaline phosphatase.

4. The method for constructing a sequencing library according to claim 1, wherein in Step (5) the oligonucleotide probe is a library of oligonucleotide probes.

5. The method for constructing a sequencing library according to claim 1, wherein in Step (2) the blunt-end repair is performed by using T4 DNA polymerase.

6. The method for constructing a sequencing library according to claim 1, wherein in Step (5) the separation marker is a biotin modification.

7. The method for constructing a sequencing library according to claim 1, wherein the long strand of linker A has a length of 40-48 bases and the short strand of linker A has a length of 9-14 bases.

* * * * *